United States Patent [19]
Ahlstrand et al.

[11] 3,970,565
[45] July 20, 1976

[54] SEPARATING AND FILTERING DEVICE

[75] Inventors: Bengt Erik Ahlstrand, Djursholm;
Rune Henry Carlsson, Sjuntorp, both of Sweden

[73] Assignee: Aktiebolaget Stille-Werner, Sweden

[22] Filed: Nov. 26, 1974

[21] Appl. No.: 527,374

[30] Foreign Application Priority Data
Nov. 27, 1973 Sweden .............................. 7316030

[52] U.S. Cl. ................................ 210/359; 210/518; 210/DIG. 23
[51] Int. Cl.² ......................................... B01D 33/00
[58] Field of Search ............... 210/77, 83, 292, 293, 210/356, 359, 437, 454, 456, 460, 483, 497, DIG. 23, DIG. 24, 514–516

[56] References Cited
UNITED STATES PATENTS

| | | | |
|---|---|---|---|
| 3,163,229 | 12/1964 | Salisbury | 210/356 UX |
| 3,508,653 | 4/1970 | Coleman | 210/DIG. 23 |
| 3,661,265 | 5/1972 | Greenspan | 210/DIG. 23 |
| 3,687,296 | 8/1972 | Spinosa et al. | 210/460 X |
| 3,814,258 | 6/1974 | Ayres | 210/DIG. 23 |
| 3,817,390 | 6/1974 | Maruniak et al. | 210/460 |
| 3,826,375 | 7/1974 | Fournier | 210/292 X |
| 3,894,952 | 7/1975 | Ayres | 210/DIG. 23 |

*Primary Examiner*—Charles N. Hart
*Assistant Examiner*—Robert H. Spitzer
*Attorney, Agent, or Firm*—Hill, Gross, Simpson, Van Santen, Steadman, Chiara & Simpson

[57] ABSTRACT

A separating and filtering device for effecting sealed separation of blood into a light phase and a heavy phase within a tubular fluid sample container comprising a cup-shaped piston having a closed bottom and a permeable side wall. The piston has axially spaced first and second sealing lips adapted to sealingly engage with the inner surface of the tubular container, and the first sealing lip is deflectable to permit passage of the lighter phase past this sealing lip on movement of the cup-shaped piston downwardly, through the lighter phase, while preventing the heavier phase from such passage.

7 Claims, 4 Drawing Figures

SEPARATING AND FILTERING DEVICE

BACKGROUND OF THE INVENTION

1. Field of the invention

This invention relates to an apparatus for effecting sealed separation of a two-phase fluid within a single container, and more specifically to the separation of blood serum or plasma from the blood cells.

2. Prior art

The U.S. Pat. No. 3,508,653, granted to Charles M. Coleman on Apr. 28, 1970, describes a container assembly for effecting sealed separation of blood into a light phase and a heavy phase. The disclosed assembly comprises a rigid tubular container adapted to receive a blood sample and housing a resilient piston in sealing contact therewith. The piston is adapted to be moved downwardly through the light phase, responsive to an applied force, while permitting upward flow of the light phase therearound. When the piston reaches the sealing region, the applied force is withdrawn, and the piston establishes a seal with the internal surface of the tubular container.

One problem inherent with the apparatus described in the patent to Coleman is that if the piston is designed so as to permit a satisfactory upward flow of the light phase therearound, then there is a hazard that the permanent seal of the piston with the internal surface of the tubular container at the sealing region is unsatisfactory. Another hazard inherent in a piston design so as to permit a satisfactory upward flow of the light phase therearound is that fibrin threads and crushed blood cells may be drawn with the light phase, past the piston, and cause problems or errors at the analysis.

Another apparatus for effecting separation of blood into a light phase and a heavy phase is described in U.S. Pat. No. 3,512,940, granted on May 19, 1970, to Justine J. Shapiro. The apparatus described in the patent to Shapiro comprises a hollow plunger acting as a piston. The plunger has a porous bottom portion serving as a filter.

One important drawback of filters of this and similar types is that although they may be able to adequately separate the light blood phase from the heavy phase, they are never able to completely prevent contamination of the serum or plasma by various constituents of the heavier phase, as time passes by.

Further, in many cases, the filter constitutes a separate body which forms a part of the piston, and, thus, the filter has to be inserted into the piston or attached thereto by a separate, time consuming and expensive step.

SUMMARY OF THE INVENTION

According to the invention there is provided a separating and filtering device for effecting sealed separation of fluid, such as blood, into a light phase and a heavy phase within a tubular container adapted to receive a fluid sample, comprising a cup-shaped piston having a closed bottom and a permeable side wall. The piston has axially spaced radially extending first and second sealing lips adapted to sealingly engage with the inner surface of said tubular container. The first sealing lip is deflectable to permit passage of the lighter phase past that sealing lip on movement of the cup-shaped piston downwardly, through the lighter phase, while preventing the heavier phase from such passage.

Preferably, the side wall has through-going axially elongated narrow slots, which widens radially inwardly, and which may be bridged by an outer ridge running uninterruptedly around the side wall, essentially midway between said lips.

According to the invention detachable push means may be provided for pushing the piston downwardly into the tubular container.

Preferably the cup-shaped piston is designed as an integral lowermost part of an upwardly open ended collection or filtrate tube having a slightly smaller outer diameter than the inner diameter of the tubular container, and, if desired, provided with exterior means for guidance thereof against the inner surface of the tubular container. Also, the collection or filtrate tube may be provided with means adapted to bear against the upper end of the tubular container to limit the depth of insertion of the collection or filtrate tube into the tubular container.

DESCRIPTION OF THE PREFERRED EMBODIMENTS

Figure 1:
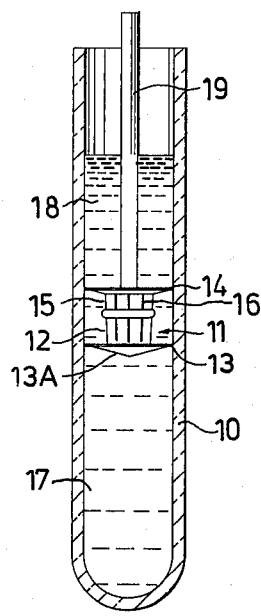
FIG. 1 illustrates one embodiment of a tubular container assembly according to the invention, partly in axial longitudinal section.

FIG. 1 illustrates a blood collection assembly comprising a blood collection tube 10 and a separating unit, generally denoted 11 disposed therein. The blood collection tube 10 is of the ordinary disposable type and has a constant internal diameter throughout its length, down to the rounded bottom thereof.

The separating unit 11 comprises a unitary sealing and filtering cup-shaped piston 12, comprising a lowermost sealing and filtering lip 13, an uppermost sealing lip 14 and an essentially cylindrical, permeable wall portion 15 extending therebetween. The cup-shaped piston 12 has a closed and tight bottom 13A from which the sealing and filtering lip 13 extends radially outwardly to run uninterruptedly circumferentially around the bottom 13A. The lip 13 is thin having a thickness of about 0.1 millimeter, and the outer diameter of the lip 13 is slightly greater than the inner diameter of the collection tube 10, so as to permit the lip 13 to form a seal with the inner surface of the collection tube 10. Of course, to enable the said sealing effect, the lip 13 must consist of a material having at least some degree of flexibility. Therefore, the lip 13 like the rest of the cup-shaped piston of which the lip forms an integral part, should consist of a suitable flexible material, such as "Nylon."

The design of the sealing lip 14, running circumferentially around the uppermost end of the cup-shaped piston portion 12, preferably is similar to that of the lip 13, but the lip 14 may be at least slightly stiffer and less flexible than the lip 13.

In use of the assembly as shown in FIG. 1, blood is collected in the tube 10 and is permitted to stand for some time in order to effect some phase separation. The tube is then placed in a centrifuge which completes separation into two phases, viz. at the bottom a heavy phase 17 which consists of the packed blood cells and fibrin threads, and disposed on top of the heavy phase will be a light phase 18 which is the serum. If plasma should be isolated, an anticoagulant must be added to prevent blood clot formation. The tube may then be centrifuged immediately, without initial separation. In that case, the lighter phase at the top of the tube will consist of plasma.

After the centrifugation, or simultaneously therewith, the unitary filtering and separating piston 12 is caused to move down the tube 10 to assume a position between the heavy phase 17 and the light phase 18 so as to isolate them permanently from each other. The piston 12 may be cause to move downwardly of the tube 10 due to its own mass by correspondingly controlling the speed of centrifugation, or the piston 12 may be pushed downwardly by means of a releasable push rod 19, FIG. 1, which is then simply thrown away.

As the piston 12 moves downwardly the lip 13 scrapes off fibrin threads and possible crushed blood cells from the inner surface of the tube 10 and moves such material downwardly into the lower portion of the tube 10. At the same time, the lip 13 deflects sufficiently to let through the light phase 18 flow past the lip 13 into the circular space around the wall 15, and from the space further on through the slots 16 into the cup-shaped piston 12 and up above the piston 12 with the downward movement thereof. The fluid that has passed the lip 13 is effectively prevented from flowing around the piston 12 by means of the uppermost lip 14 which sealingly engages with the inner surface of the tube 10. Also, as the piston 12 moves downwardly, the uppermost lip 14 has a scraping action to further clean the inner surface of the tube from possible residues left by the lip 13.

The slots 16 are so narrow that they effectively prevent any fibrin threads and blood cells, that may have passed the lip 13, from being drawn with the lighter phase up into the uppermost portion of the tube 10.

As soon as the downward movement of the piston 12 is stopped, an effective seal is provided between the two phases, on one hand by means of the closed wall with its lip 13, which seal the heavy phase 17 from the fluid in the space around the wall 15, and on the other by means of the filtering wall 15 and the lip 14 therearound, which seal the light phase 18, from the small quantity of fluid around the wall 15. Thus, it will be seen, that the light phase 18 is filtered twice, i.e. first when passing the lip 13 and secondly when passing through the permeable wall 15.

Figure 3:
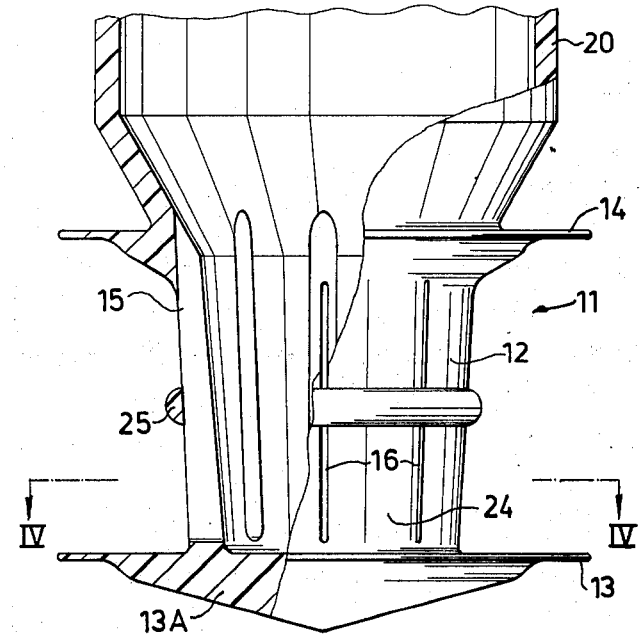
FIG. 3 illustrates, to an enlarged scale, and partly in axial longitudinal section, the lowermost portion of the piston used in the assembly in FIG. 2.
Figure 2:
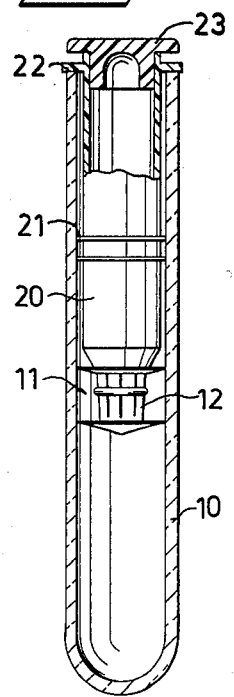
FIG. 2 illustrates a second embodiment of a tubular container assembly according to the invention, similarly partly in axial longtitudinal section.
Figure 4:
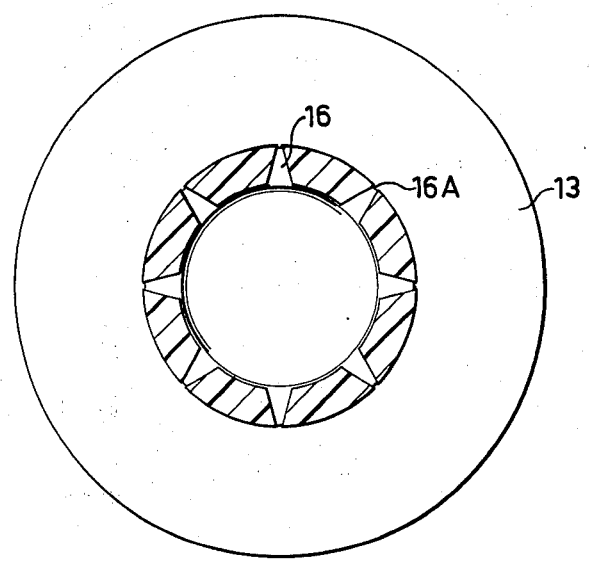
FIG. 4 is a cross-sectional view of the lowermost piston portion in FIG. 3 as seen from plane IV—IV in FIG. 3.

The embodiment as shown in FIGS. 2–4 is similar to the one shown in FIG. 1, with the exception that in FIGS. 2–4 the cup-shaped piston 12 is formed as an integral part of a collection filtrate or tube 20 of a slightly smaller outer diameter than the inner diameter of the tube 10.

Also in this embodiment the essentially cylindrical wall 15 extending between the two lips 13 and 14 is permeable in that, in the example shown, it is provided with a plurality of axially elongated through-going narrow slots 16. As seen in cross-sections of the cup-shaped piston 12, FIG. 4, these slots 16 are somewhat triangular to present only a narrow inlet opening 16A to the inflowing serum or plasma whereas the slots widens radially inwardly, in part to prevent clogging, and in part, which may be more important, to readily permit withdrawal of the tool member used to impart the internal shape to the cup-shaped piston during manufacture thereof. For the last mentioned reason, i.e. to readily permit withdrawal of the internal tool member, the inner surface of the essentially cup-shaped piston 12 should preferably be somewhat tapering axially.

The collecting or filtrate tube 20 extends integrally from the upper rim of the cup-shaped piston 12 the piston 12 having a slightly smaller outer diameter than the inner diameter of the tube 10. The tube 20 is open ended and may have exteriorly thereof one or more circumferential flanges 21 for guidance of the filtrate or collection tube 20 as it is moved downwardly into the tube 10, or may it have axial ribs for the same purpose. The tube 20 may be provided with one or more abutments, such as a ring flange 22, to bear against the upper end of the tube 10 to prevent the filtration or collection tube's 20 going to go down into the tube 10 deeper than to a predetermined depth. Preferably, the collection filtrate or tube 20 has, at the upper end thereof, a suitable cap member 23, which is preferably designed so as to readily permit insertion of a needle for withdrawal of the desired sample quantity from a lighter phase for analysis purposes.

As will be seen from FIGS. 3 and 4 the ribs 24, between which the narrow slots 16 are formed, are comparatively thin. For that reason it may be advantageous to provide the wall portion 15 with at least one circumferential, uninterrupted ridge 25 intermediate the ends of the ribs 24 to prevent deflections of said ribs 24 to such an extent that the filtering effect of side wall 15 would be jeoparized.

What we claim is:
1. A separating and filtering device for effecting sealed separation of a fluid, such as blood, into a light phase and a heavy phase, comprising:
   a. a tubular container for receiving a sample of the fluid having both phases;
   b. a cup-shaped hollow piston disposed in said container and having a closed bottom and a radially permeable side wall; and
   c. a first and a second circumferential sealing lip extending radially from said piston and axially spaced apart by said permeable side wall, said lips normally sealingly engaging the inner surface of said tubular container, said first lip being adjacent to said closed bottom and being deflectable to enable only the light phase to pass by in response to any downward movement of said piston.

2. A device as claimed in claim 1 wherein the permeability of said side wall is provided by through-going axially elongated narrow slots sized to block flow of fibrin threads and blood cells.

3. A device as claimed in claim 2 wherein said narrow slots widen radially inwardly.

4. A device as claimed in claim 2 wherein said narrow slots are bridged by an outer ridge running uninterruptedly around said side wall, substantially midway between said lips.

5. A device as claimed in claim 1 wherein said cup-shaped piston is an integral lowermost part of an upwardly open ended filtrate tube having a slightly smaller outer diameter than the inner diameter of the tubular container.

6. A device as claimed in claim 5 wherein said filtrate tube has radially projecting exterior means for guidance thereof against the inner surface of the tubular container.

7. A device as claimed in claim 5 wherein said filtrate tube has means adapted to bear against the upper end of the tubular container to limit the depth of insertion of the filtrate tube into the tubular container.

* * * * *